(12) United States Patent
Sykes et al.

(10) Patent No.: US 7,368,582 B2
(45) Date of Patent: May 6, 2008

(54) AMIDOMETHYL-SUBSTITUTED 2-(4-SULFONYLAMINO)-3-HYDROXY-3,4-DIHYDRO-2H-CHROMEN-6-YL COMPOUNDS, A PROCESS AND INTERMEDIATES FOR THEIR PRODUCTION, AND PHARMACEUTICAL COMPOSITIONS CONTAINING THEM

(75) Inventors: David Sykes, Didcot (GB); Brian Moloney, Didcot (GB); Lester Marrison, Didcot (GB); Dieter Ziegler, Hemmingen (DE); Michael Mlinaric, Hannover (DE); Christiane Boecker, Hannover (DE); Reinhard Brueckner, Hannover (DE); Michael Weske, Burgdorf (DE); Klaus Witte, Hannover (DE); Yvan Fischer, Barsinghausen (DE)

(73) Assignee: Solvay Pharmaceuticals GmbH, Hannover (DE)

( * ) Notice: Subject to any disclaimer, the term of this patent is extended or adjusted under 35 U.S.C. 154(b) by 255 days.

(21) Appl. No.: 10/961,368

(22) Filed: Oct. 12, 2004

(65) Prior Publication Data
US 2005/0148659 A1 Jul. 7, 2005

Related U.S. Application Data

(60) Provisional application No. 60/536,505, filed on Jan. 15, 2004.

(30) Foreign Application Priority Data
Oct. 17, 2003 (DE) ................... 103 48 298

(51) Int. Cl.
*C07D 311/00* (2006.01)
(52) U.S. Cl. .................................... 549/399
(58) Field of Classification Search ............. 549/404, 549/399
See application file for complete search history.

(56) References Cited

U.S. PATENT DOCUMENTS

| 5,191,092 | A | 3/1993 | Niewöhner et al. |
| 5,637,739 | A | 6/1997 | Jacobsen et al. |
| 5,663,393 | A | 9/1997 | Jacobsen et al. |
| 5,811,448 | A | 9/1998 | Englert et al. |
| 5,955,607 | A | 9/1999 | Brendel et al. |
| 6,071,953 | A * | 6/2000 | Lang et al. ............ 514/457 |
| 6,150,356 | A | 11/2000 | Lloyd et al. |
| 6,177,449 | B1 | 1/2001 | Brendel et al. |
| 6,191,164 | B1 | 2/2001 | Lang et al. |
| 6,221,866 | B1 | 4/2001 | Brendel et al. |
| 6,511,977 | B1 | 1/2003 | Lloyd et al. |
| 2004/0058931 | A1 | 3/2004 | Lloyd et al. |
| 2004/0067944 | A1 | 4/2004 | Lloyd et al. |

FOREIGN PATENT DOCUMENTS

| EP | 0 425 946 A2 | 8/1991 |
| EP | 0 807 629 A1 | 11/1997 |
| EP | 0 860 440 A1 | 8/1998 |
| EP | 0 905 131 A1 | 3/1999 |
| EP | 0 906 911 A1 | 4/1999 |
| JP | 2000-336085 | 12/2000 |
| WO | WO 91/14694 | 10/1991 |
| WO | WO 00/12077 | 3/2000 |
| WO | WO 00/14084 | 3/2000 |
| WO | WO 00/58300 | 10/2000 |
| WO | WO 01/00573 A1 | 1/2001 |

OTHER PUBLICATIONS

Gregory J. Amos et al., "Differences between outward currents of human atrial and subepicardial ventricular myocytes," Journal of Physiology (1996), 491.1, pp. 31-50.
Christine Beeton et al., "Selective Blocking of Voltage-Gated $K^+$ Channels Improves Experimental Autoimmune Encephalomyelitis and Inhibits T Cell Activation[1]," The Journal of Immunology, pp. 936-944.
Torill Berg, "Analysis of the pressor response to the $K^+$ channel inhibitor 4-aminopyridine," European Journal of Pharmacology 452 (2002), 325-337.
Thomas E. DeCoursey et al., "Voltage-gated $K^+$ channels in human T lymphocytes: a role in mitogenesis?," Nature, vol. 307, Feb. 1984, pp. 465-468.
Margarita Garcia-Calvot et al., "Purification, Characterization, and Biosynthesis of Margatoxin, a Component of *Centruroides margaritatus* Venom That Selectively Inhibits Voltage-dependent Potassium Channels," The Journal of Biological Chemistry, vol. 268, No. 25, Issue of Sep. 5, pp. 18866-18874, 1993.
Eric N. Jacobsen, "Asymmetric Catalysis of Epoxide Ring-Opening Reactions," Acc. Chem. Res. 2000, 33, pp. 421-431.

(Continued)

*Primary Examiner*—D. Margaret Seaman
*Assistant Examiner*—Nizal Chandrakumar
(74) *Attorney, Agent, or Firm*—Crowell & Moring LLP

(57) ABSTRACT

Compounds corresponding to formula I:

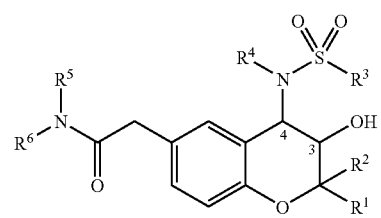

in which $R^1$, $R^2$, $R^3$, $R^4$, $R^5$ and $R^6$ have the meanings given in the description; a process for the preparation of these compounds; intermediate products used to prepare such compounds, and pharmaceutical compositions containing such compounds.

11 Claims, No Drawings

OTHER PUBLICATIONS

Jianlin Feng et al., "Antisense Oligodeoxynucleotides Directed Against Kv1.5 mRNA Specifically Inhibit Ultrarapid Delayed Rectifier K sup + Current in Cultured Adult Human Atrial Myocytes," Ovid: Feng: Circ Res, vol. 80(4), Apr. 1997, pp. 572-579.

William Hu et al., "Depolarization-Induced $^{86}Rb^{30}$ Efflux in CHO Cells Expressing a Recombinant Potassium Channel," Journal of Pharmacological and Toxicological Methods 34, 1-7 (1995), pp. 1-7.

Paul M. Kerr et al., "Heteromultimeric Kv1.2-Kv1.5 Channels Underlie 4-Aminopyridine-Sensitive Delayed Rectifier $K^+$ Current of Rabbit Vascular Myocytes," Circulation Research, Nov. 23, 2001, pp. 1038-1044.

Gloria C. Koo et al., "Blockade of the Voltage-Gated Potassium Channel Kv1.3 Inhibits Immune Responses in Vivo$^1$," Gloria C. Koo et al., The Journal of Immunology, pp. 5120-5128.

Gui-Rong Li, "Evidence for Two Components of Delayed Rectifier $K^{plus}$ Current in Human Ventricular Myocytes," Ovid: Li: Circ Res, vol. 78(4), Apr. 1996, pp. 689-696.

Jaromir Plášk et al., "Slow fluorescent indicators of membrane potential: a survey of different approaches to probe reponse analysis," Journal of Photochemistry and Photobiology B: Biology 33 (1996) 101-124.

Dan M. Roden, MD, "Current Status of Class III Antiarrhythmic Drug Therapy," The American Journal of Cardiology, vol. 72, Aug. 26, 1993, pp. 44B-49B.

Gemot Schram et al., "Differential Distribution of Cardiac Ion Channel Expression as a Basis for Regioanl Specialization in Electrical Function," Circulation Research, May 17, 2002, pp. 939-950.

Dirk J. Snyders, "Structure and function of cardiac potassium channels," Cardiovascular Research 42 (1999) 377-390.

Julius Gy. Papp et al., "Effect of Bertosamil on Atrial and Ventricular Threshold for Fibrillo-Flutter in Comparison with Quinidine in Anaesthetized Cats," Pharmacological Research, vol. 25, Supplement 2, 1992, pp. 156-157.

Robert H. Spencer et al., "Immunological Indentification of the *Shaker*-Related Kv1.3 Potassium Channel Protein in T and B Lymphocytes, and Detection of Related Porteins in Flies and Yeast," Biochemical and Biophysical Research Communications, pp. 201-206.

L. Szekeres et al., "Mechanism of Increased Susceptibility to Fibrillation of the Hypothermic Mammalian Heart in Situ," Brit. J. Pharmacol. (1961), 17, 167-175.

Schotten, U. et al., "Loss of atrial contractility is primary cause of atrial dilatation during first days of atrial fibrillation", AJP-Heart Circ Physiol, vol. 287, Nov. 2004, pp. H2324-H2331.

Manning, W. J. et al., "Impaired Left Atrial Mechanical Function After Carioversion: Relation to the Duration of Atrial Fibrillation", JACC, vol. 23, No. 7, Jun. 1994, pp. 1535-1540.

* cited by examiner

AMIDOMETHYL-SUBSTITUTED 2-(4-SULFONYLAMINO)-3-HYDROXY-3,4-DIHYDRO-2H-CHROMEN-6-YL COMPOUNDS, A PROCESS AND INTERMEDIATES FOR THEIR PRODUCTION, AND PHARMACEUTICAL COMPOSITIONS CONTAINING THEM

BACKGROUND OF THE INVENTION

The present invention relates to novel amidomethyl-substituted 2-(4-sulfonylamino)-3-hydroxy-3,4-dihydro-2H-chromen-6-yl derivatives with a potassium channel-blocking effect, in particular with an effect influencing the cardiovascular system, and also to medicaments containing these compounds. Furthermore, the invention relates to a process for the preparation of the novel compounds and intermediate products of this process.

Indanes, benzopyrans and analogues of such compounds which have potassium channel-blocking effects, and in particular effects beneficially influencing the cardiovascular system, are known from U.S. Pat. No. 6,150,356 (=WO 00/12077).

Published international application no. WO 00/58300 discloses chroman derivatives which are suitable as medicaments, in particular antiarhythmically effective medicaments.

SUMMARY OF THE INVENTION

It was an object of the present invention to provide new pharmaceutically active substances useful for treating disease conditions.

Another object of the invention was to provide active substances useful in treating cardiovascular diseases, especially cardiac arrhythmias.

A further object of the invention was to provide pharmaceutically active substances characterized by high effectiveness and patient tolerability.

It is also an object of the invention to provide active substances which exhibit an antiarrhythmic activity with a marked atrial-selective activity profile.

These and other objects have been achieved in accordance with the present invention by providing a compound corresponding to formula I:

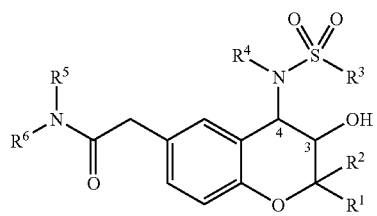

wherein
$R^1$ is $C_{1-4}$-alkyl,
$R^2$ is $C_{1-4}$-alkyl,
$R^3$ is phenyl which is optionally substituted 1 or 2 times by halogen, $C_{1-4}$-alkyl, $C_{1-4}$-alkoxy or trifluoromethyl; naphthyl or biphenyl,
$R^4$ is hydrogen; $C_{1-6}$-alkyl or $C_{3-7}$-cycloalkyl-$C_{1-4}$-alkyl,
$R^5$ is hydrogen, and
$R^6$ is $C_{1-6}$-alkyl; phenyl-$C_{1-4}$-alkyl, the phenyl group of which is optionally substituted once by halogen; furyl-$C_{1-4}$-alkyl or tetrahydronaphthyl, or
$R^5$ and $R^6$, together with the nitrogen to which they are bonded, form a piperazine ring which may optionally be substituted by phenyl.

It has now surprisingly been found that a group of novel amidomethyl-substituted 2-(4-sulfonylamino)-3-hydroxy-3,4-dihydro-2H-chromen-6-yl compounds according to the invention possess potassium channel-blocking properties and are suitable for the treatment of cardiovascular diseases, preferably for the treatment of cardiac arrhythmias. The compounds according to the invention are distinguished by high effectiveness with good compatibility and in the case of anti-arrhythmic action also by a marked atrial-selective action profile. In addition, the compounds according to the invention have properties which lead one to expect an additional effect influencing the immune system.

The invention thus relates to novel amidomethyl-substituted 2-(4-sulfonylamino)-3-hydroxy-3,4-dihydro-2H-chromen-6-yl compounds corresponding to formula I:

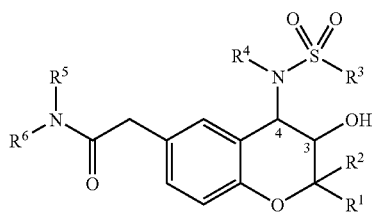

wherein
$R^1$ is $C_{1-4}$-alkyl,
$R^2$ is $C_{1-4}$-alkyl,
$R^3$ is phenyl, which is optionally substituted 1 to 2 times by halogen, $C_{1-4}$-alkyl, $C_{1-4}$-alkoxy or trifluoromethyl; naphthyl or biphenyl,
$R^4$ is hydrogen; $C_{1-6}$-alkyl or $C_{3-7}$-cycloalkyl-$C_{1-4}$-alkyl,
$R^5$ is hydrogen, and
$R^5$ is $C_{1-6}$-alkyl; phenyl-$C_{1-4}$-alkyl, the phenyl group of which is optionally substituted once by halogen; furyl-$C_{1-4}$-alkyl or tetrahydronaphthyl, or
$R^5$ and $R^6$, together with the nitrogen to which they are bonded, form a piperazine ring which may optionally be substituted by phenyl.

Furthermore, the invention relates to pharmaceutical compositions containing the compounds of Formula I. Furthermore, the invention relates to a process for the preparation of the compounds of Formula I and to intermediate products of this process.

Whenever the compounds of Formula I or other compounds described within the context of the present invention include substituents consisting of or comprising $C_{1-4}$-alkyl or $C_{1-6}$-alkyl groups, these groups may each be straight-chain or branched.

$R^1$ and $R^2$ preferably each have the meaning methyl.

$R^3$ preferably has the meaning phenyl which is optionally substituted 1 to 2 times by halogen, $C_{1-4}$-alkyl, $C_{1-4}$-alkoxy or trifluoromethyl. In particular, $R^3$ has the meaning of phenyl substituted once by $C_{1-4}$-alkyl. Where $R^3$ is halogen-substituted phenyl, fluorine, chlorine, bromine and iodine are considered as halogen. As a particularly preferred meaning, $R^3$ stands for 4-ethylphenyl.

R[4] is preferably hydrogen, $C_{1-6}$-alkyl or cyclopropyl-$C_{1-4}$-alkyl, in particular cyclopropylmethyl. Where R[4] stands for $C_{1-6}$-alkyl, this is in particular branched and preferably represents neopentyl, 2,2-dimethylbutyl, 2-ethylbutyl, 3-methylbutyl or 2-methylpropyl.

R[5] is preferably hydrogen.

R[6] preferably has the meanings phenyl-$C_{1-4}$-alkyl, in particular benzyl or phenethyl, or the meaning tetrahydronaphthyl, in particular 1-tetrahydronaphthyl. (R)-1-tetrahydronaphthyl is preferred.

Particularly preferred compounds of Formula I are selected from the group consisting of:

2-(4-{[(4-ethylphenyl)sulfonyl]amino}-3-hydroxy-2,2-dimethyl-3,4-dihydro-2H-chromen-6-yl)-N-1,2,3,4-tetrahydronaphth-1-yl acetamide;

2-((3S,4R)-4-{[(4-ethylphenyl)sulfonyl]amino}-3-hydroxy-2,2-dimethyl-3,4-dihydro-2H-chromen-6-yl)-N-[(1R)-1,2,3,4-tetrahydronaphth-1-yl]acetamide;

N-benzyl-2-{4-[[(4-ethylphenyl)sulfonyl](neopentyl)amino]-3-hydroxy-2,2-dimethyl-3,4-dihydro-2H-chromen-6-yl}acetamide;

2-{4-[[(4-ethylphenyl)sulfonyl](neopentyl)amino]-3-hydroxy-2,2-dimethyl-3,4-dihydro-2H-chromen-6-yl}-N-(2-phenylethyl)acetamide, and 2-(4-{[(4-methylphenyl)sulfonyl]amino}-3-hydroxy-2,2-dimethyl-3,4-dihydro-2H-chromen-6-yl)-N-1,2,3,4-tetrahydronaphth-1-yl acetamide.

According to the invention, the novel compounds of Formula I are obtained by reacting a compound corresponding to formula II:

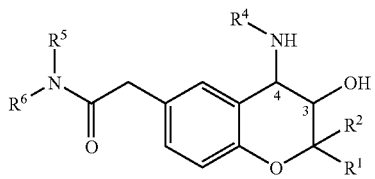

wherein R[1], R[2], R[4], R[5], and R[6] have the above meanings, with a compound corresponding to formula III:

wherein R[3] has the above meaning and X is a cleavable leaving group. The reaction can be carried out using a conventional wet-chemical process in an organic solvent which is inert under the reaction conditions, in particular a dipolar-aprotic solvent such as dichloromethane or in a mixture of such solvents and in the presence of a base. Suitable bases include non-nucleophilic organic nitrogen bases such as tertiary lower alkylamines, for example triethylamine. Liquid organic bases used in excess can also be used as solvents. If desired, the reaction can be catalyzed by a known coupling aid such as 4-N,N-dimethylaminopyridine (=DMAP). Suitable reaction temperatures are between room temperature and 80° C., for example 65° C. Suitable reaction pressures are between normal pressure and approximately 200 bar, for example 180 bar. If the compound of Formula III which is used is liquid, it may be advantageous to remove the solvent used from the reaction mixture after the addition of the compound of Formula III to the compound of Formula II dissolved in the solvent in known manner, for example at reduced pressure. Whenever in the starting compounds of Formula II R[4] stands for hydrogen, it is advantageous to use equimolar amounts of compound of Formula III. Usually halogen, preferably chlorine or bromine, is used as leaving group X in compounds of Formula III.

Furthermore, the reaction of a compound of Formula II with a compound of Formula III can also be performed in known manner on a solid phase, in particular on a reactive resin such as aminomethyl polystyrene (AMPS). This reaction variant can preferably be used for the preparation of smaller amounts of substance, for example on a scale of 1 to 10 mmol. Where synthesis is on a solid phase, preferably a readily filterable base such as known polymer-supported methylpiperidine (=PS methylpiperidine) can be used as base. Suitable reaction temperatures for solid-phase synthesis are between 10° C. and 40° C., preferably room temperature. Compounds of Formula I may be isolated in known manner from the reaction mixture and if necessary purified in known manner.

Compounds of Formula II can be prepared by reacting an epoxide compound corresponding to formula IV:

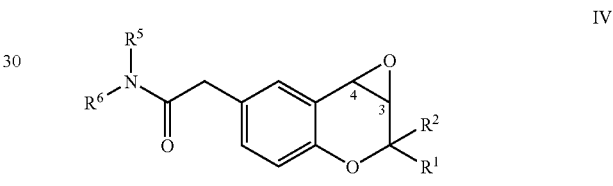

wherein R[1], R[2], R[5] and R[6] have the above meanings, in known manner with a nucleophilic organic nitrogen compound, preferably ammonia in aqueous solution, in a dipolar-protic solvent such as a lower-alkyl alcohol, preferably ethanol. Suitable reaction temperatures are between room temperature and 60° C.

Where compounds of Formula II are desired in which R[4] represents $C_{1-6}$-alkyl or $C_{3-7}$-cycloalkyl-$C_{1-4}$-alkyl, the resulting compound of Formula II, in which R[4] represents hydrogen, can then be alkylated in known manner. The alkylation can be carried out in particular as an aminoalkylation, by first reacting the compound of Formula II, in which R[4] stands for hydrogen, with an aldehyde corresponding to formula V:

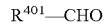

wherein $R^{401}$ is hydrogen, $C_{2-5}$-alkyl or $C_{3-7}$-cycloalkyl-$C_{0-3}$-alkyl, and then reducing the resulting imine intermediate product by addition of a reducing agent to the alkylamine compound of Formula II. Examples of suitable reducing agents include complex borohydrides such as $NaBH_3CN$ or known polymer-supported borohydride (=PS—$BH_4$).

In a first variant, the reaction can be carried out in a polar-protic organic solvent which is inert under the reaction conditions, in particular methanol, the reduction of the imine being performed in situ without isolating it in the same solvent. Suitable reaction temperatures for this variant are between room temperature and 60° C., for example 50° C. In a second variant, the reaction of the compound of Formula II, wherein $R^4$ stands for hydrogen, with an aldehyde of Formula V to form the imine intermediate product can be carried out in a dipolar-aprotic solvent, in particular tetrahydrofuran (=THF). In that case, it is advantageous to add catalytic amounts of a hydrophilic agent, for example an orthoester, in particular trimethyl orthoformate (=TMOF), to speed up the reaction. Then the imine intermediate product can be isolated and taken up in a polar-protic solvent stated above for the first variant, in order to perform the reduction in this solvent. This second variant may preferably be carried out at room temperature. In the nucleophilic ring-opening reaction of epoxides of Formula IV described above in two variants, as a rule compounds of Formula II are obtained in which the vicinal substituents in position 3 and in position 4 of the pyran ring, namely the hydroxyl group and the amino group, are each in the trans position to one another.

The compounds of Formula II are themselves novel compounds which are advantageously suitable as intermediate products for the preparation of novel pharmacologically active substances, for example for the preparation of the compounds of Formula I.

Compounds of Formula III and compounds of Formula V are known per se or can be prepared in known manner from known compounds.

Compounds of Formula IV can be prepared by reacting a compound corresponding to formula VI:

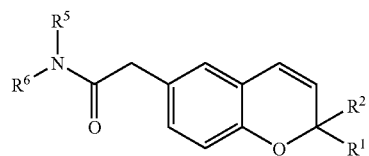

VI wherein $R^1$, $R^2$, $R^5$ and $R^6$ have the above meanings, in known manner with a peroxide compound capable of epoxide formation, preferably with m-chloroperbenzoic acid (MCPBA), in an organic polar-aprotic solvent which is inert under the reaction conditions, preferably dichloromethane, and in the presence of a base. An example of a particularly suitable base is an aqueous solution of sodium hydrogen carbonate. The reaction may preferably be carried out at room temperature.

Compounds of Formula I have at least in the vicinal carbon atoms in position 3 and in position 4 of the pyran ring in each case an asymmetric center or chiral center and can therefore occur in several isomeric forms. The invention includes both the isomerically pure compounds of Formula I and mixtures of these isomers. The optically active compounds of Formula I can be obtained, for example, from the mixtures of the isomers of Formula I or from mixtures of the isomers of Formula II in known manner, e.g. by chromatographic separation on chiral separating materials. Mixtures of the isomers of Formula II can also be obtained by reaction with suitable optically active acids, e.g. camphorsulfonic acid or D- or L-tartaric acid, and subsequent fractionation into the respective optical antipodes by fractional crystallization of the resulting salts.

The optically active compounds of Formula I can also be prepared directly by chiral synthesis. Where compounds of Formula I are to be prepared wherein the hydroxy substituent in position 3 of the pyran ring and the $R^4NSO_2R^3$-substituent in position 4 of the pyran ring are in a stereochemically defined trans position to one another, in each case the starting point may be epoxides of Formula IV in which the appropriate stereochemistry is already predetermined. Epoxides of Formula IV with correspondingly predetermined stereochemistry can for example be prepared by epoxidizing alkenes of Formula VI in known manner with the aid of a chiral catalyst in accordance with the method of Jacobsen, U.S. Pat. No. 5,637,739 (=EP 521,099). Where for example a compound of Formula I is to be prepared in which the chiral center in position 3 of the pyran ring is in the S configuration and in which the chiral center in position 4 of the pyran ring is in the R configuration, an intermediate product of Formula VI can be reacted in the presence of a chiral catalyst, in particular (S,S)-manganese (III) salen and in the presence of an oxygen donor, in particular sodium hypochlorite in aqueous solution, in an organic solvent which is inert under the reaction conditions, in particular dichloromethane. The reaction may advantageously be carried out at a pH value between 9.5 and 11.5. To set a suitable pH value, preferably a buffer consisting of $Na_2HPO_4$ and pyridine-N-oxide can be added to the reaction mixture. Suitable reaction temperatures are between $-10°$ C. and room temperature, preferably at $0°$ C. Where a compound of Formula I is to be prepared in which the chiral center in position 3 of the pyran ring is in the R configuration and in which the chiral center in position 4 of the pyran ring is in the S configuration, the procedure can be analogous to the directions described above, but (R,R)-manganese (III) salen is then used instead of (S,S)-manganese (III) salen.

Compounds of Formula VI can be prepared by reacting a compound corresponding to formula VIII:

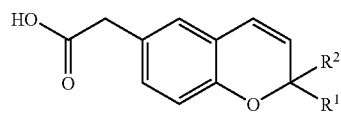

VII wherein $R^1$ and $R^2$ have the above meanings, with a compound corresponding to formula VIII:

 VIII wherein $R^5$ and $R^8$ have the above meanings, in a manner known for aminoacylation. The carboxylic acids of Formula VII or their reactive derivatives such as acid halides, in particular acid chlorides or acid bromides, may be used as acylation agents. If the acids of Formula VII themselves are used as acylation agents, the reaction thereof with the amino compounds of Formula VIII can advantageously also be carried out in the presence of a known coupling reagent, for example 1,1-carbonyldiimidazole, ethyl chloroformate or an alkyl carbodiimide, e.g. N'-(3-dimethylaminopropyl)-N-ethylcarbodiimide (=EDC), or a cycloalkyl carbodiimide such as dicyclohexylcarbodiimide. The acylation may take place in an organic solvent which is inert under the reaction conditions at temperatures from $-30°$ C. to $+50°$ C., preferably at room temperature. Suitable solvents include halogenated hydrocarbons such as dichloromethane and cyclic ethers such as tetrahydrofuran or dioxane or mixtures of these solvents.

Compounds of Formula VII can be prepared by hydrolyzing the ester group of a compound corresponding to formula IX:

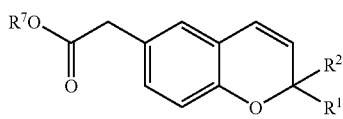

wherein $R^1$ and $R^2$ have the above meanings, and $R^7$ is $C_{1-4}$-alkyl, in known manner. The hydrolysis can be carried out, for example, in a polar-protic solvent such as ethylene glycol by contacting with a base, for example a strong base such as dilute aqueous sodium hydroxide solution. Suitable reaction temperatures are between room temperature and the boiling point of the solvent or of the solvent mixture.

Compounds of Formula IX can be prepared by reacting a compound corresponding to formula X:

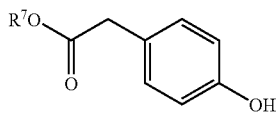

wherein $R^7$ has the above meaning, with a compound corresponding to formula XI:

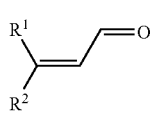

wherein $R^1$ and $R^2$ have the above meanings, in known manner. The reaction can be carried out in an organic solvent which is inert under the reaction conditions, such as toluene or xylene and in the presence of an acid with water being separated by azeotropic distillation. Examples of suitable acids include acetic acid or propionic acid. Advantageously, the reaction is carried out with the addition of a catalyst such as a Lewis acid, for example phenylboronic acid. Suitable reaction temperatures are between room temperature and the boiling point of the solvent or of the solvent mixture, for example around 120° C.

The compounds of Formula X and Formula XI are known per se or can be prepared in known manner from known compounds.

The advantageous effects of compounds of Formula I as pharmacologically active substances will become apparent from the following background. It is already known that substances which block endogenous cardiac potassium channels can be used as active substances to counter cardiovascular diseases, in particular to counter cardiac arrhythmias. By blocking outward-directed potassium currents in the heart, a prolongation of the action potential of the heart can be brought about which has a beneficial effect on antiarrhythmic heart conditions. Examples of this known treatment are Class III antiarrhythmic drugs.

One problem of such non-specific potassium channel blockers is their low degree of selectivity with respect to their effect on different heart tissues. Thus for a relatively long time it has been assumed that in particular Class III antiarrhythmic drugs can lead to undesirable prolongation of the QT interval in the electrocardiogram (=ECG) and to polymorphic ventricular tachycardias ("torsades de pointes"), which can trigger ultimately undesirable complications such as for example ventricular fibrillation. For this reason, potassium channel blockers have been sought which are capable of selectively influencing the potassium currents of the atrium, but not of the ventricle. Since the $K_v$ 1.5-potassium channels in the heart which were discovered some time ago are located exclusively in the atrium, but not in the ventricle, it can be assumed that these $K_v$ 1.5-potassium channel-blocking compounds are suitable as atrial-selective antiarrhythmic drugs. $K_v$ 1.5-potassium channels and other potassium channels are however located not only in the heart, but e.g. also in vessels of the body. Therefore it cannot always be ruled out that $K_v$ 1.5-potassium channel-blocking compounds may lead to increases in blood pressure resulting from the blockade of potassium channels in the vessels. $K_v$ 1.5-potassium channel-blocking compounds which are free of side-effects which raise blood pressure are therefore preferred. Further undesirable side-effects which may occur on administration of many $K_v$ 1.5-potassium channel-blocking compounds are additional Class I-antiarrhythmic side-effects and also negatively inotropic effects.

The compounds of Formula I are distinguished by an effect which particularly pronouncedly and selectively blocks the cardiac $K_v$ 1.5-potassium channels. In addition to particularly good effectiveness and a marked atrial-selective antiarrhythmic activity profile, the compounds of Formula I at most have slight undesirable side-effects such as increase in blood pressure, Class I-antiarrhythmic side-effects and negatively inotropic effects. The compounds of Formula I are therefore indicated for the treatment and/or prophylaxis of cardiovascular diseases, in particular atrial fibrillation, atrial flutter and other cardiac arrhythmias, in larger mammals and humans.

Furthermore, the compounds of Formula I exhibit a clear effect of blocking the $K_v$ 1.3-potassium channels. $K_v$ 1.3-potassium channels are preferentially located in cells of the immune system. A connection is made between blockade of the $K_v$ 1.3-potassium channels and inter alia an anti-proliferative and/or immunosuppressive effect (cf. C. Beeton et al., The Journal of Immunology 166 (2001) 936-944). It can therefore be assumed of compounds which are capable of blocking $K_v$ 1.3-potassium channels—for example the compounds of Formula I—that they are also suitable for the treatment and/or prophylaxis of proliferative, chronic inflammatory and autoimmune diseases such as multiple sclerosis.

DESCRIPTION OF PHARMACOLOGICAL TEST METHODS

The cited example numbers relate to the subsequent preparation examples.

1. In-Vitro Investigation of the $K_v$ 1.5-Potassium Channel-Blocking Effect of the Substances The $K_v$ 1.5-potassium channel-blocking effect of the substances was demonstrated in a known test model or analogously to this test model (cf. W. Hu et al., J. Pharmacol.

Toxicol. Methods 34 (1995) 1-7). In this test model, a cell line of egg cells of the Chinese hamster (="Chinese hamster oocytes", "CHO") is used which originates from a single cell and stably expresses the $K_v$ 1.5-channel. By incubation overnight in a nutrient medium containing RbCl or a "loading buffer" (all values in mM: RbCl 5, NaCl 140, $CaCl_2$ 2, $MgSO_4$ 1, HEPES buffer 10, glucose 5) the aforementioned oocytes are loaded with $Rb^+$ under the influence of $Na^+/K^+$-ATPase. Thereafter, a portion of the oocytes is incubated as a reference standard in the absence of an inhibitor, while another portion of the oocytes is incubated in the presence of the respective inhibitory test substance of Formula I. Then the oocytes are depolarized by increasing the extracellular potassium-ion concentration, which causes the $K_v$ 1.5-potassium channels of the oocytes to open. In the absence of an inhibitor, the $Rb^+$ ions flow through the $K_v$ 1.5-potassium channels into the liquid surrounding them. In the presence of an inhibitory test substance of Formula I, on the other hand, the $Rb^+$ ions remain locked within the oocytes. The extent of the $K_v$ 1.5-potassium channel-blocking effect of the test substances of Formula I is determined by measuring the $Rb^+$ ion concentration in the liquid surrounding them by means of atomic absorption spectroscopy against a reference standard.

Chinese hamster oocytes (see above) were cultivated in a known, RbCl-containing nutrient medium for CHO-cells and placed in the sample wells of a 96-sample capacity sample plate ("96 well plate"). The oocytes were allowed to grow overnight in order to obtain monolayers of the oocytes. Then the nutrient medium was pipetted off, and each sample well was washed three times with 100 µl portions of a preincubation buffer of low potassium-ion concentration (all values in mM: KCl 5, NaCl 140, $CaCl_2$ 2, $MgSO_4$ 1, HEPES buffer 10, glucose 5). Then 50 µl of a solution of the respective test substance (stock solution in DMSO, dilution with preincubation buffer, final concentration in the test batch 10 µM) or of the solvent (as negative controls) was added to each sample well and incubated for 10 min. in each case at room temperature. Then 50 µl of a stimulation buffer with elevated potassium-ion concentration (KCl 145 mM, NaCl 0 mM, otherwise as preincubation buffer) was added to each sample well and the samples were then incubated for a further 10 min. at room temperature. In each case, 80 µl of the liquid surrounding the oocytes from each sample well was then transferred separately to the sample wells of an analysis sample plate, and the $Rb^+$ ion concentration in the liquids was determined by atomic absorption spectroscopy. The test substances were each double-tested. The signal section which represented the $K_v$ 1.5 component of the $Rb^+$ outflow was defined by using as positive control the known potassium channel blocker 4-AP in a high concentration ($100 \times IC_{50}$ for the $K_v$ 1.5 channel). This made it possible to determine which portion of the $Rb^+$ outflow was dependent on the influence of the 4-AP and therefore is to be assigned to the $K_v$ 1.5 channel. For the substances which in the concentration of 10 µM used led to a reduction in the $Rb^+$ outflow of at least 50%, additional tests were performed with lower concentrations of the test substances in order to be able to determine the half-maximum effective concentration. In each case the concentration of half-maximum inhibition of the test substances of Formula I ($IC_{50}$) was given as characteristic variable.

In this test model the test substances of Formula I listed in the following Table 1 had the $IC_{50}$ values given in the table.

TABLE 1

$K_v$1.5-potassium channel-blocking effect of the test substances in vitro

| Example No. | $IC_{50}$ |
|---|---|
| 2 | 2.0 |
| 4 | 1.6 |
| 5 | 5.0 |
| 6 | 2.9 |
| 7 | 1.5 |
| 8 | 0.5 |
| 9 | 2.9 |
| 10 | 1.6 |
| 11 | 3.2 |
| 12 | 3.2 |
| 13 | 6.5 |
| 15 | 4.0 |
| 16 | 6.3 |
| 17 | 2.65 |
| 18 | 2.7 |
| 19 | 2.5 |
| 21 | 3.3 |
| 22 | 3.4 |
| 23 | 4.3 |
| 24 | 5 |
| 25 | 5.2 |
| 26 | 5.2 |
| 27 | 5.6 |

2. In-Vitro Investigation of the $K_v$ 1.3-Potassium Channel-Blocking Effect of the Substances The $K_v$ 1.3-potassium channel-blocking effect of the substances was demonstrated in a known test model (e.g. from Genion, Hamburg) or analogously to this test model (cf. J. Plásek and Sigler, J. Photochem. Photobiol. 33 (1996) 101-124). In this test model, known oocytes of the Chinese hamster (=CHO) are used which are stably transfected with the $K_v$ 1.3-potassium channel. The blockade of the cell-inherent $K_v$ 1.3-potassium channel activity in the transfected cells is accompanied by a positive shift in the membrane potential from approx. −40 mV to −30 mV, whereas in the wild-type CHO cells investigated in parallel no significant shift in the membrane potential is triggered. A change in the membrane potential is thus connected to the reduction in the $K_v$ 1.3-potassium channel activity. By blocking the $K_v$ 1.3-potassium channels e.g. with substances of Formula I and the resulting change in the membrane potential, an accumulation of a membrane potential-sensitive fluorescent dye in intracellular compartments of the oocytes and ultimately increasing fluorescence occurs. The change in the membrane potential of the oocytes is therefore measured indirectly via the increase in fluorescence of the membrane potential-senstive dyes.

The cells were transfected with the $K_v$ 1.3 plasmid in known manner with a commercially obtainable transfection reagent (DMRIE-C from Gibco BRL, Germany). The successful transfection was verified by immunofluorescence and by "patch-clamp" investigations of the potassium ion current. The fluorescence measurements were performed on a Tecan Safire fluorescence reader from Tecan, Germany. In each case, the increase in the fluorescent intensity caused by the blockade of the $K_v$ 1.3-potassium channels in the oocytes with substances of Formula I in a concentration of 10 µM was determined as characteristic variable. The increase in the fluorescent intensity was given in each case in percent (%) compared with an increase in the fluorescent intensity caused by the reference substance margatoxin. Margatoxin is known as a selective $K_v$ 1.3-potassium channel blocker (see e.g. M. Garcia-Calvo et al., J. Biol. Chem. 268 (1993) 18866-18874).

In this test model the test substances of Formula I listed in the following Table 2 had the percentages given in the table:

TABLE 2

$K_v$1.3-potassium channel-blocking effect of the test substances in vitro

| Example No. | Increase in the fluorescent intensity (% margatoxin) |
|---|---|
| 2 | 72 |
| 5 | 82 |
| 6 | 97 |
| 9 | 107 |
| 10 | 82 |
| 11 | 99 |
| 12 | 111 |
| 13 | 53 |
| 17 | 72 |
| 18 | 141 |
| 19 | 171 |
| 21 | 86 |
| 22 | 71 |
| 23 | 41 |

3. Investigation of the Functional Effectiveness of the Substances on the Atrium of Rats' Hearts in Vitro The functional antiarrhythmic effectiveness of the substances was demonstrated in the test model set forth below. In this test model it is determined to what extent the $K_v$ 1.5-blocking substances of Formula I result in a prolongation of the functional refractory period in the left atrium of rats. The refractory period is the minimum possible elapsed time between the basic stimulus and additional stimulus in which a renewed contraction can be triggered. The extent of the prolongation of the functional refractory period is a measurement of the antiarrhythmic effectiveness of the substances according to the invention. The functional refractory period is determined by testing on the electrically stimulated preparation at what elapsed time from the preceding contraction a renewed contraction can be triggered by additional electrical stimuli.

The hearts were removed from freshly sacrificed rats (Sprague-Dawley, Charles-River, Germany). The left atria were isolated and fastened to force transducers in a temperature-controlled (30° C.), gasified ($O_2$ 95%, $CO_2$ 5%) organ bath which was filled with modified Tyrode solution (all values in mM: NaCl 137; KCl 2.7; $CaCl_2$ 1.8; $MgCl_2$ 0.8; $NaHCO_3$ 11.9; $NaH_2PO_4$ 0.6; glucose 5). In order to trigger regular contractions, the preparations were electrically stimulated (rectangular pulses, pulse magnitude 3.5× threshold stimulus, pulse width 1.5 ms, frequency 1 Hz). Initially, the initial value of the functional refractory period was determined by applying extra pulses in addition to the basic stimulus, the elapsed time from the preceding basic stimulus being shortened until no further additional contraction could be triggered. Then the cumulative addition of increasing concentrations (0.1-10 μM) of the substances of Formula I took place at intervals of 20 min. each, the refractory period being determined again in each case 18 min. after the addition had taken place. Before the measurement, stock solutions of the test substances (3.2 and 0.32 mM in 100% DMSO) were prepared. In order to achieve the desired final concentrations of the substances (0.1-10 μM) in the organ bath (volume 100 ml), corresponding volumes of these stock solutions were then poured into the organ bath.

In each case the prolongation of the functional refractory period (FRP) in the left atrium of the rats' hearts in milliseconds observed after the addition of 10 μM of the respective substance of Formula I to the atrial preparations was given as characteristic variable.

In this test model the test substances of Formula I listed in the following Table 3 exhibited the prolongations of refractory period given in the table, with higher values representing a stronger antiarrhythmic effectiveness:

TABLE 3

FRP-prolonging effect of the test substances (10 μM) on the left atria of rats' hearts in vitro

| Example No. | FRP prolongation [ms] |
|---|---|
| 1 | 15 |
| 2 | 20 |
| 4 | 17 |
| 7 | 24 |
| 8 | 17 |
| 9 | 30 |
| 10 | 20 |
| 11 | 24 |
| 12 | 14 |
| 13 | 28 |
| 14 | 22 |
| 15 | 30 |
| 16 | 20 |

4. Investigation of the Functional Effectiveness of the Substances on Guinea-Pig Hearts in Vivo In the test model shown below, it was shown that the substances according to the invention at most have slight undesirable proarrhythmic effects on repolarization in the ventricle. To this end, the influence of the compounds of Formula I on the effective refractory period (ERP) and other influencing variables on guinea-pig hearts in vivo were investigated. In this test model, non-selective potassium channel blockers not in accordance with the invention, which also block HERG and/or $K_v$LQT1 channels, result in undesirable prolongation of the ERP and the QT time on an electrocardiogram (=ECG). The QT time is likewise a measurement of the repolarization in the heart. Prolongations of both the ERP and the QT time, respectively, which are due to the substances were independently interpreted as indications of the risk of the occurrence of undesirable torsade-de-pointes arrhythmias. Furthermore, the QRS interval also was determined in each case from the ECG as a measurement of the ventricular rate of spread of stimulus. Even a prolongation of the QRS interval caused by a test substance is connected with an increased risk of undesirable pro-arrhythmic side-effects. Therefore in this test model the lack of an ERP and QT time prolongation signifies a low risk, but the occurrence of a relevant ERP and QT prolongation on the other hand signifies an elevated risk of undesirable pro-arrhythmic effects. Also the lack of a prolongation of the QRS interval which is due to the substances due to the substances of Formula I investigated indicates a low risk of undesirable pro-arrhythmic side-effects, since lack of QRS prolongation indicates an undisturbed spread of stimulus in the ventricle. Conversely, a QRS prolongation, which is typically triggered by Class I antiarrhythmic drugs indicates slowing of the conduction rate and may promote the occurrence of ventricular tachycardias to ventricular fibrillation.

Male guinea pigs (Dunkin-Hartley from Charles River) were anaesthetized (ketamine 50 mg/kg, xylazine 10 mg/kg) and each of them was provided with a venous access via one jugular vein for administration of compounds of Formula I or a vehicle. A bipolar stimulation catheter was fed into the right ventricle of the guinea pigs via the other jugular vein (stimulation frequency 5 Hz). The arterial blood pressure was measured by a catheter located in the carotid artery which was connected to a Statham pressure transducer. The ECG was recorded via needle electrodes. The measured data were digitized via an analog/digital converter, recorded on a computer with suitable software (Ponemah Physiology Platform from Gould, USA) and printed out in parallel on a multichannel printer. After an equilibration period of 45 min., increasing doses of the compounds of Formula I or of the vehicle were administered intravenously (=i.v.) to the guinea pigs at 12-minute intervals. Before the first administration and in each case one minute after administration of increasing doses (0.1–max. 30 µmole/kg) of the substances of Formula I, the effective refractory period was measured. For this, after five normal stimuli in each case an additional pulse was applied and the elapsed time thereof from the preceding pulse was increased until a heart action was triggered. The observed time interval corresponds to the ERP of the ventricular myocardium.

In order to detect possible effects of the test substances on the blood pressure, in the same test model after each administration of substance the systolic and diastolic blood pressure was determined and compared with the previous blood-pressure level. The parameters were recorded automatically 1 and 8 min. after each administration of substance. Table 4 also shows changes in systolic blood pressure due to the compounds of Formula I given below (minus effects due to the vehicle). None of the compounds listed resulted in a significant blood pressure increase.

In this test model, the test substances of Formula I listed in the following Table 4 had the effects given in the table. Only statistically significant effects were listed, with a t-test with a significance limit of P<0.05 being used for the statistical testing. In Table 4, the indication "n.s." (="not statistically significant") means that the substance of the corresponding example does not have any statistically significant influence on the measured variable listed.

TABLE 4

Effect of the test substances (1 min. after administration of 10 µmole/kg i.v.) on the ERP, QT and QRS intervals in the ventricle of guinea pigs and simultaneously measured changes in the systolic blood pressure in vivo (n.s. = not statistically significant, negative values indicate shortening or reduction)

| Ex. No. | ERP (ms) | QT (ms) | QRS (ms) | syst. blood pressure (mm Hg) |
|---|---|---|---|---|
| 1 | n.s. | n.s. | n.s. | n.s. |
| 2 | n.s. | n.s. | n.s. | n.s. |
| 4 | n.s. | n.s. | n.s. | n.s. |
| 7 | −8.2 | n.s. | n.s. | −15.3 |
| 8 | n.s. | n.s. | n.s. | −10.7 |
| 10 | −8.0 | n.s. | n.s. | −15.9 |
| 11 | n.s. | n.s. | n.s. | n.s. |
| 12 | n.s. | n.s. | n.s. | n.s. |
| 13 | n.s. | n.s. | n.s. | n.s. |
| 16 | −7.5 | n.s. | n.s. | −8.6 |

5. Investigation of the Functional Effectiveness of the Substances on the Hearts of Anaesthetised Cats in Vivo In the test model shown below, it was shown that the substances according to the invention at most have a marked atrial-selective effect on the heart. After administration of the substances according to the invention, a significant increase in the atrial fibrillation threshold—i.e. the current intensity at which atrial fibrillation occurs—was observed. At the same time, on the other hand, the ventricular fibrillation threshold is influenced only minimally.

Living cats were anaesthetised with chloralose/urethane (50/300 mg/kg i.v.) and were ventilated with ambient air. Then, following thoracotomy, stimulating electrodes were attached to the right atrium and the ventricle. The atrial and ventricular fibrillation threshold was determined in known manner by administration of rectangular pulses of increasing current intensity until atrial or ventricular fibrillation occurred (for performance see in detail: Br. J. Pharmac. 17 (1961) 167; Hdb. exp. Pharmacol. XVI/3 (1975) 131; Pharmacol. Res. 25 Suppl. 2 (1992) 156). The test substances of Formula I were dissolved in propylene glycol (80%) and administered intravenously in increasing doses (5-30 µmol/kg). Atrial and ventricular fibrillation thresholds were then determined at 5-minute intervals in known manner after the addition of the respective dose. The increase in the respective fibrillation threshold due to the substances investigated was expressed in percent of the value before administration of substance, i.e. a doubling of the fibrillation threshold corresponds to an increase of 100%.

In this test model, the test substances of Formula I listed in the following Table 5 had the effects given in the table.

TABLE 5

Increase in the atrial (AFT) and ventricular fibrillation threshold (VFT) in anaesthetized cats in vivo (dose 30 µmol/kg i.v.)

| Ex. No. | AFT (%) | VFT (%) | Selectivity factor (AFT:VFT) |
|---|---|---|---|
| 1 | 66 | 22 | 3 |
| 2 | 261 | 15 | 17 |
| 4 | 226 | 19 | 12 |
| 9 | 213 | 29 | 7 |
| 10 | 241 | 19 | 13 |

The particularly good physiological tolerability of the compounds according to the invention can also be demonstrated in further pharmacological test models. Thus for example it can be demonstrated in an in vitro test on cardiac muscle preparations of guinea pigs that the compounds of Formula I at most have slight Class I-side-effects. antiarrhythmic side-effects. Furthermore, it can be demonstrated in an in vitro model on rats' hearts and in another in vitro model on guinea pigs' hearts that the compounds of Formula I at most cause slight negatively inotropic effects.

The compounds of Formula I may be administered in conventional pharmaceutical preparations. In an individual case, special dosage forms may be indicated. The doses to be used may vary individually and will naturally vary depending on the type of condition to be treated and the substance used. In general, however, pharmaceutical dosage forms with an active substance content of 0.2 to 500 mg, in particular 10 to 200 mg, active substance per individual dose are suitable for administration to humans and larger mammals. The compounds may be contained according to the invention, together with conventional pharmaceutical auxiliaries and/or carriers, in solid or liquid pharmaceutical preparations. Examples of solid preparations include preparations which can be administered orally, such as tablets, coated tablets, capsules, powders or granules, or alternatively suppositories. These preparations may contain conventional pharmaceutical inorganic and/or organic carriers, such as talcum, lactose or starch, in addition to conventional pharmaceutical auxiliaries, for example lubricants or tablet disintegrating agents. Liquid preparations such as suspensions or emulsions of the active substances may contain the usual diluents such as water, oils and/or suspension agents such as polyethylene glycols and the like. Other auxiliaries may additionally be added, such as preservative, taste correctives and the like.

The active substances may be mixed and formulated with the pharmaceutical auxiliaries and/or carriers in known manner. For the preparation of solid medicament forms, the active substances may for example be mixed with the auxiliaries and/or carriers in conventional manner and may be wet or dry granulated. The granules or powder may be poured directly into capsules or be pressed into tablet cores in conventional manner. These may be coated in known manner if desired.

The following examples are intended to illustrate the invention further, without limiting its scope.

EXAMPLE 1

2-(4-{[(4-Ethylphenyl)sulfonyl]amino}-3-hydroxy-2,2-dimethyl-3,4-dihydro-2H-chromen-6-yl)-N-1,2,3,4-tetrahydronaphth-1-yl acetamide

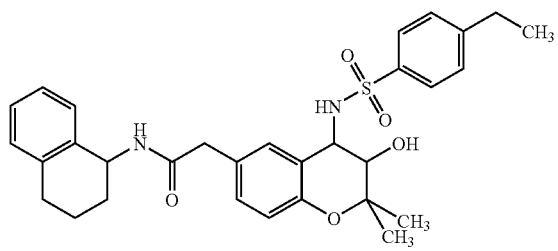

A) 25 g methyl-4-hydroxyphenylacetate, 14.5 ml 3-methylbut-2-enal and 18.3 g phenylboronic acid were placed together under nitrogen atmosphere in 1 l dry toluene and heated to boiling for 7 hours under reflux cooling. Then 60 ml glacial acetic acid was added to this receiving solution at room temperature (=RT) and the mixture was again heated to boiling for 7 hours under reflux cooling. It was allowed to cool to room temperature, the solvent was largely evaporated at reduced pressure and the remaining residue was poured into 300 ml of a 1:1 (v/v) mixture of ethyl acetate (=EA) and water. The pH value was adjusted to 5 by addition of solid sodium bicarbonate, the organic phase was separated off and largely evaporated at reduced pressure. Chromatography of the remaining residue on silica gel (mobile phase: petroleum ether/EA 10:1 v/v) yielded 16 g methyl-(2,2-dimethyl-2H-chromen-6-yl)acetate as pale yellow oil.

$^1$H-NMR (400 MHz, CDCl$_3$) δ [ppm]: 1.15 (s, 3H) 1.27 (t, 3H) 1.43 (s, 3H) 1.60-1.85 (3H) 1.97 (m, 1H) 2.66-2.82 (4H) 3.20-3.29 (3H) 3.54 (dd, 1H) 4.23 (dd, 1H) 5.06 (m, 1H) 5.28 (d, 1H) 5.59 (d, 1H) 6.55 (d, 1H) 6.66 (d, 1H) 6.97 (dd, 1H) 7.03-7.18 (4H) 7.35 (m, 2H) 7.87 (m, 2H); $^{13}$C-NMR (101 MHz, CDCl$_3$) δ [ppm]: 15.1 (q) 18.5 (q) 20.1 (t) 26.6 (q) 28.8 (t) 29.2 (t) 30.2 (t) 42.9 (t) 47.7 (d) 55.1 (d) 74.8 (d) 78.7 (s) 117.9 (d) 121.3 (s) 126.3 (d) 127.2 (s) 127.4 (d, 3 C) 128.2 (d) 128.8 (d) 128.9 (d, 2 C) 129.3 (d) 130.3 (d) 136.5 (s) 137.6 (s) 137.7 (s) 150.2 (s) 152.3(s) 170.3 (s).

B) 46 g of the methyl-(2,2-dimethyl-2H-chromen-6-yl) acetate obtained above (total amount from several analogous batches), 150 ml ethylene glycol and 400 ml of a 20%-strength aqueous sodium hydroxide solution were heated to boiling for 3 hours in 440 ml tetrahydrofuran (=THF) under reflux cooling. Then the resulting mixture was allowed to cool to room temperature, the solvent was largely evaporated at reduced pressure, and 200 ml tert. butylether and 300 ml water were added to the remaining residue. It was stirred for 10 min. and then the aqueous phase was acidulated by addition of a 20%-strength aqueous hydrochloric acid solution to pH 6. The aqueous phase was extracted twice with 300 ml portions of dichloromethane and the combined organic phases were dried over 20 g sodium sulfate. The solvent was largely evaporated at reduced pressure, petroleum ether was added to the remaining residue, and a first resulting crystal fraction was filtered out from the solvent. The filtrate was concentrated again at reduced pressure, with another crystal fraction being produced. The combined crystal fractions were dried and 33.8 g 2,2-(dimethyl-2H-chromen-6-yl)acetic acid was obtained, which was used without further purification for the subsequent reaction.

$^1$H-NMR (400 MHz, CDCl$_3$) δ [ppm]: 1.41 (s, 6H) 3.52 (s, 2H) 5.59 (d, 1H) 6.27 (d, 1H) 6.72 (d, 1H) 6.88 (d, 1H) 6.99 (dd, 1H); $^{13}$C-NMR (101 MHz, CDCl$_3$) δ [ppm]: 28.1 (q, 2 C) 40.2 (t) 76.3 (s) 116.5 (d) 121.4 (s) 122.1 (d) 125.3 (s) 127.2 (d) 129.9 (d) 131.1 (d) 152.3 (s) 177.8 (s).

C) 9.6 g 1,1-carbonyldiimidazole (=CDI) dissolved in 85 ml THF was slowly added to a solution of 11.7 g of the 2,2-dimethyl-2H-chromen-6-yl acetic acid obtained above in 100 ml THF and stirred for 30 min. at room temperature. 8.8 ml 1,2,3,4-tetrahydro-1-naphthylamine, dissolved in 30 ml THF, was dropped slowly into this receiving solution, the resulting mixture was stirred for 1 hour and left to stand overnight at room temperature. The solvent was largely evaporated at reduced pressure, and the remaining residue was stirred with a mixture of diethyl ether and isopropanol (100:1 v/v) and crystallized. The resulting crystals were removed by suction and dried at 65° C. and 20 bar. Chromatography of the diethyl ether/isopropanol washing liquid on silica gel yielded further intermediate product, which was combined with the main quantity and dried. 17.5 g 2-(2,2-dimethyl-2H-chromen-6-yl)-N-1,2,3,4-tetrahydronaphth-1-yl acetamide was obtained as colorless solid, which was used without further purification for the subsequent reaction.

$^1$H-NMR (400 MHz, CDCl$_3$) δ [ppm]: 1.41 (s, 6H) 1.60-1.85 (3H) 1.98-2.08 (1H) 2.65-2.80 (2H) 3.45-3.55 (2H) 5.12-5.20 (1H) 5.60 (d, 1H) 5.66 (d, 1H) 6.26 (d, 1H) 6.71 (d, 1H) 6.86 (d, 1H) 6.96 (dd, 1H) 7.02-7.07 (1H) 7.08-7.17 (3H); $^{13}$C-NMR (101 MHz, CDCl$_3$) δ [ppm]: 20.2 (t) 28.0 (q, 2 C) 29.2 (t) 30.3 (t) 43.2 (t) 47.7 (d) 76.3 (s) 116.8 (d) 121.7 (s) 122.0 (d) 126.2 (d) 126.9 (s) 127.2 (d) 128.2 (d) 129.1 (d) 129.8 (d) 131.3 (d) 136.7 (s) 137.5 (s) 152.2 (s) 170.7 (s).

D) 950 ml of a saturated aqueous sodium hydrogen carbonate solution was added to a solution of 11 g of the 2-(2,2-dimethyl-2H-chromen-6-yl)-N-1,2,3,4-tetrahydronaphth-1-yl acetamide obtained above in 600 ml dichloromethane. A total of 15 g m-chloroperoxybenzoic acid (=MCPBA) in three 5 g portions was added to this receiving solution at 5 min. intervals, and the mixture was stirred for 18 hours at room temperature. The organic phase was separated and substantially entirely evaporated on a rotary evaporator at 65° C. and 20 bar. 2-(2,2-dimethyl-1a,7b-dihydro-2H-oxireno[c]chromen-6-yl)-N-1,2,3,4-tetrahydronaphth-1-yl acetamide was obtained as crude oil, which was used without further purification for the subsequent reaction.

$^1$H-NMR (400 MHz, CDCl$_3$) δ [ppm]: 1.23 (s, 6H) 1.56 (s, 6H) 1.63-1.85 (6H) 1.97-2.10 (2H) 2.65-2.82 (4H) 3.43-3.56 (6H) 3.84-3.89 (2H) 5.12-5.22 (2H) 5.62-5.72 (2H) 6.75 (d, 1H) 6.76 (d, 1H) 7.02-7.19 (10H) 7.23-7.27 (2H); $^{13}$C-NMR (101 MHz, CDCl$_3$) δ [ppm]: 20.1 (t) 22.6 (q) 25.7 (q) 29.2 (t) 30.2 (t) 43.1 (t) 47.7 (d) 50.8 (d) 62.7 (d) 73.2 (s) 118.6 (d) 120.5 (s) 126.2 (d) 126.3 (d) 127.2 (d) 127.3 (d) 127.5 (s) 128.2 (d) 128.3 (d) 129.2 (d) 130.5 (d) 131.1 (d) 131.2 (d) 136.5 (s) 137.5 (s) 137.6 (s) 151.8 (s) 170.4 (s).

E) 88 ml of a 25%-strength aqueous ammonia solution was added to a solution of 16 g of the 2-(2,2-dimethyl-1a,7b-dihydro-2H-oxireno[c]chromen-6-yl)-N-1,2,3,4-tetrahydronaphth-1-yl acetamide obtained above in 88 ml ethanol, and the mixture was stirred for 18 hours at room temperature. Then 200 ml dichloromethane and 50 ml methanol were added thereto, and the mixture was stirred for a further 15 minutes. Then 200 ml water was added and the mixture was again stirred for 15 minutes. The organic phase was separated and largely evaporated at reduced pressure. The remaining residue was stirred with 30 ml of ethyl acetate, filtered and dried on a rotary evaporator at 70° C. and 20 bar. 3.1 g 2-(4-amino-3-hydroxy-2,2-dimethyl-3,4-dihydro-2H-chromen-6-yl)-N-1,2,3,4-tetrahydronaphth-1-yl acetamide was obtained as grey solid, which was used without further purification for the subsequent reaction.

$^1$H-NMR (400 MHz, DMSO-D$_6$) δ [ppm]: 1.08 (s, 6H) 1.35 (s, 6H) 1.60-1.95 (12H) 2.63-2.83 (4H) 3.17 (d, 2H) 3.32-3.40 (4H) 3.49 (d, 2H) 4.90-4.98 (2H) 5.32-5.38 (2H) 6.62 (d, 2H) 7.01 (dd, 2H) 7.05-7.18 (8H) 7.47 (d, 2H) 8.32-8.35 (2H); $^{13}$C-NMR (101 MHz, DMSO-D$_6$) δ [ppm]: 18.6 (q) 19.9 (t) 27.0 (q) 28.7 (t) 29.8 (t) 41.7 (t) 46.2 (d) 50.8 (d) 76.6 (d) 77.8 (s) 115.6 (d) 125.5 (s) 125.6 (d) 125.7 (d) 126.5 (d) 127.9 (s) 128.0 (d) 128.1 (d) 128.3 (d) 128.4 (d) 128.6 (d) 136.9 (s) 137.5 (s) 150.5 (s) 169.8 (s).

F) 1.67 g 4-ethyl benzenesulfonyl chloride was added dropwise to a solution of 3.75 g of the 2-(4-amino-3-hydroxy-2,2-dimethyl-3,4-dihydro-2H-chromen-6-yl)-N-1,2,3,4-tetrahydronaphth-1-yl acetamide obtained above and 8.4 ml triethylamine in 160 ml dichloromethane. In addition 5 ml of dimethyl formamide (=DMF) was added, and the resulting mixture was stirred for 18 hours at room temperature. Then 100 ml water was added, and the mixture was stirred for another 5 minutes. The organic phase was separated, and the solvent was evaporated at reduced pressure. The remaining residue was chromatographed on silica gel (mobile phase: ethyl acetate/cyclohexane/methanol 110:140:2 v/v/v), and the product phases were combined and reduced in volume. The residue was stirred with petroleum ether/diethyl ether 10:1 v/v. The resulting crystals were removed by suction and dried on a rotary evaporator at 40° C. and 25 bar. 2.3 g of the title compound was obtained as colorless crystals.

$^1$H-NMR (400 MHz, CDCl$_3$) δ [ppm]: m 1.14 (s, 3H) 1.16 (s, 3H) 1.26 (t, 3H) 1.28 (t, 3H) 1.44 (s, 6H) 1.60-1.85 (8H) 1.95-2.08 (2H) 2.66-2.83 (8H) 3.18-3.33 (6H) 3.53-3.63 (2H) 4.18-4.28 (2H) 5.02-5.13 (2H) 5.26-5.37 (2H) 5.52-5.60 (2H) 6.54 (d, 2H) 6.66-6.71 (2H) 6.95-7.19 (m, 10H) 7.34-7.39 (4H) 7.85-7.92 (4H); $^{13}$C-NMR (101 MHz, CDCl$_3$) δ [ppm]: 15.1 (q) 18.4 (q) 20.1 (t) 26.6 (q) 28.8 (t) 29.2 (t) 30.2 (t) 42.9 (t) 47.7 (t) 47.8 (d) 55.1 (d) 74.9 (d) 75.0 (d) 78.6 (s) 78.7 (s) 118.0 (d) 121.0 (s) 126.2 (d) 126.3 (d) 127.2 (s) 127.4 (d) 128.2 (d) 128.8 (d) 128.9 (d) 129.2 (d) 129.3 (d) 130.3 (d) 136.5 (s) 137.6 (s) 150.3 (s) 152.3 (s) 170.3 (s).

EXAMPLE 2

2-((3S,4R)-4-{[(4-ethylphenyl)sulfonyl]amino}-3-hydroxy-2,2-dimethyl-3,4-dihydro-2H-chromen-6-yl)-N-[(1R)-1,2,3,4-tetrahydronaphth-1-yl]acetamide

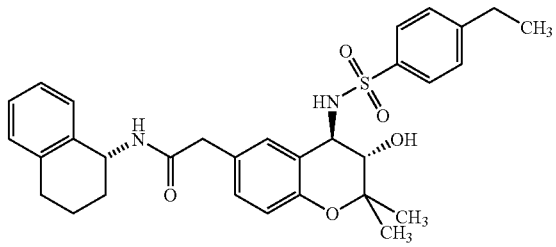

A) 24.5 g CDl, 30 g 2,2-(dimethyl-2H-chromen-6-yl) acetic acid (for preparation see Example 1B)) and 22.8 ml (1R)-1,2,3,4-tetrahydro-1-naphthylamine were reacted according to the procedure set forth in Example 1C). 49 g 2-(2,2-dimethyl-2H-chromen-6-yl)-N-[(1R)-1,2,3,4-tetrahydronaphth-1-yl]acetamide was obtained as colorless crystals, which was used without further purification for the subsequent reaction.

$^1$H-NMR (400 MHz, CDCl$_3$) δ [ppm]: 1.41 (s, 6H) 1.60-1.85 (3H) 1.98-2.08 (1H) 2.65-2.80 (2H) 3.45-3.55 (2H) 5.12-5.20 (1H) 5.60 (d, 1H) 5.66 (d, 1H) 6.26 (d, 1H) 6.71 (d, 1H) 6.86 (d, 1H) 6.96 (dd, 1H) 7.02-7.07 (1H) 7.08-7.17 (3H); $^{13}$C-NMR (101 MHz, CDCl$_3$) δ [ppm]: 20.2 (t) 28.0 (q, 2 C) 29.2 (t) 30.3 (t) 43.2 (t) 47.7 (d) 76.3 (s) 116.8 (d) 121.7 (s) 122.0 (d) 126.2 (d) 126.9 (s) 127.2 (d) 128.2 (d) 129.1 (d) 129.8 (d) 131.3 (d) 136.7 (s) 137.5 (s) 152.2 (s) 170.7 (s).

B) 5 g (S,S)-manganese-(III)-salen and 7 g pyridine-N-oxide were added to a solution of 44 g of the 2-(2,2-dimethyl-2H-chromen-6-yl)-N-[(1R)-1,2,3,4-tetrahydronaphth-1-yl]acetamide obtained above in 800 ml dichloromethane. The resulting receiving solution was cooled to 0° C., and a mixture of 660 ml of an aqueous sodium hypochlorite solution (Cl>13%) and 88 ml of a 9%-strength aqueous solution of Na$_2$HPO$_4$ were added over 45 minutes. Stirring was continued for a further 3 hours at 0° C., then the organic phase was separated and stirred for 1 hour with 500 g Celite® 503. The solid was filtered out and the filtrate was washed with dichloromethane until it was colorless. The filtrate was evaporated to dryness at reduced pressure. 40 g 2-[(1aS,7bS)-(2,2-dimethyl-1a,7b-dihydro-2H-oxireno[c]chromen-6-yl]-N-1,2,3,4-tetrahydronaphth-1-yl acetamide was obtained as crude oil, which was used without further purification or characterization for the subsequent reaction.

C) 40 g of the 2-[(1aS,7bS)-(2,2-dimethyl-1a,7b-dihydro-2H-oxireno[c]chromen-6-yl]-N-1,2,3,4-tetrahydronaphth-1-yl acetamide obtained above and 250 ml of a 25%-strength aqueous ammonia solution were reacted in a manner corresponding to the procedure of Example 1E). Chromatography of the crude product on silica gel (mobile phase: dichloromethane/methanol/25%-strength aqueous ammonia solution (75:50:2 v/v/v)) yielded 13.2 g 2-[(3S,4R)-4-amino-3-hydroxy-2,2-dimethyl-3,4-dihydro-2H-chromen-6-yl]-N-[(1R)-1,2,3,4-tetrahydronaphth-1-yl]acetamide as oil, which was used without further purification for the subsequent reaction.

$^1$H-NMR (400 MHz, DMSO-D$_6$) δ [ppm]: 1.08 (s, 6H) 1.35 (s, 6H) 1.60-1.95 (12H) 2.63-2.83 (4H) 3.17 (d, 2H) 3.32-3.40 (4H) 3.49 (d, 2H) 4.90-4.98 (2H) 5.32-5.38 (2H) 6.62 (d, 2H) 7.01 (d, 2H) 7.05-7.18 (8H) 7.47 (d, 2H) 8.32-8.35 (2H); $^{13}$C-NMR (101 MHz, DMSO-D$_6$) δ [ppm]: 18.6 (q) 19.9 (t) 27.0 (q) 28.7 (t) 29.8 (t) 41.7 (t) 46.2 (d) 50.8 (d) 76.6 (d) 77.8 (s) 115.6 (d) 125.5 (s) 125.6 (d) 125.7 (d) 126.5 (d) 127.9 (s) 128.0 (d) 128.1 (d) 128.3 (d) 128.4 (d) 128.6 (d) 136.9 (s) 137.5 (s) 150.5 (s) 169.8 (s).

D) 5.94 ml 4-ethyl benzenesulfonyl chloride, 13.2 g of the 2-[(3S,4R)-4-amino-3-hydroxy-2,2-dimethyl-3,4-dihydro-2H-chromen-6-yl]-N-[(1R)-1,2,3,4-tetrahydronaphth-1-yl]acetamide obtained above, 88 ml triethylamine and 4 ml dimethyl formamide were reacted in a manner corresponding to the procedure of Example 1F). 6.2 g of the title compound was obtained as solid, amorphous foam.

$^1$H-NMR (400 MHz, CDCl$_3$) δ [ppm]: 1.15 (s, 3H) 1.26 (t, J=7.6 Hz, 3H) 1.45 (s, 3H) 1.60-1.85 (3H) 2.01 (m, 1H) 2.65-2.82 (4H) 3.20-3.33 (3H) 3.58 (dd, J=9.0, 3.0 Hz, 1H) 4.23 (dd, J=9.0, 8.7 Hz, 1H) 5.04 (m, 1H) 5.16 (d, J=8.7 Hz, 1H) 5.51 (d, J=8.5 Hz, 1H) 6.54 (d, J=2.0 Hz, 1H) 6.68 (d, J=8.4 Hz, 1H) 6.98 (dd, J=8.4, 2.0 Hz, 1H) 6.95-7.19 (4H) 7.37 (m, 2H) 7.87 (m, 2H); $^{13}$C-NMR (101 MHz, CDCl$_3$) δ [ppm]: 15.1 (q) 18.4 (q) 20.1 (t) 26.6 (q) 28.9 (t) 29.2 (t) 30.2 (t) 43.0 (t) 47.8 (d) 55.1 (d) 75.0 (d) 78.7 (s) 118.0 (d) 121.1 (s) 126.2 (d) 127.3 (s) 127.4 (d, 3 C) 128.2 (d) 128.7 (d) 129.0 (d, 2 C) 129.3 (d) 130.4 (d) 136.5 (s) 137.6 (s) 137.7 (s) 150.4 (s) 152.3 (s) 170.3 (s); $[α]_D^{20}$=−8.3° (c=0.1, MeOH).

EXAMPLE 3

N-benzyl-2-{4-[[(4-ethylphenyl)sulfonyl](neopentyl)amino]-3-hydroxy-2,2-dimethyl-3,4-dihydro-2H-chromen-6-yl}acetamide

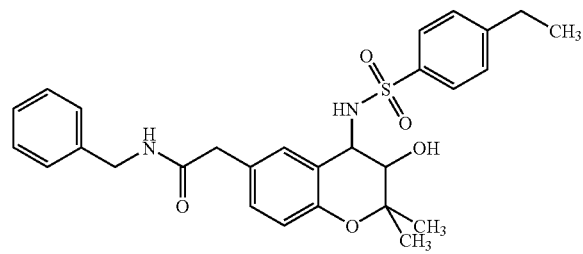

A) 16.2 g of CDI dissolved in 300 ml tetrahydrofuran (THF) was slowly added to a solution of 19.7 g 2,2-dimethyl-2H-chromen-6-yl)acetic acid (for preparation see Example 1B)) in 300 ml THF and stirred for 10 minutes at room temperature. 10.9 ml benzylamine was added slowly dropwise to this receiving solution, and the resulting mixture was stirred for 1 hour. The solvent was largely evaporated at reduced pressure, and the remaining residue was extracted once with 500 ml of a mixture of ethyl acetate and water (2:3 v/v). The organic phase was largely evaporated at reduced pressure, and the remaining residue was chromatographed on silica gel (mobile phase: EA/cyclohexane 1:1 v/v). Drying of the product fractions on a rotary evaporator at 70° C. and 20 bar yielded 28 g N-benzyl-2-(2,2-dimethyl-2H-chromen-6-yl)acetamide as oil, which was used without further purification or characterization for the subsequent reaction.

B) 980 ml of a saturated aqueous sodium hydrogen carbonate solution was added to a solution of 28 g of the N-benzyl-2-(2,2-dimethyl-2H-chromen-6-yl)acetamide obtained above in 480 ml dichloromethane. A total of 44.1 g MCPBA in three 14.7 g portions was added to this receiving solution at 5 min. intervals, and the mixture was stirred for 18 hours at room temperature. The organic phase was separated, extracted once with 200 ml of a saturated aqueous sodium hydrogen carbonate solution, and the organic phase was then substantially completely evaporated at reduced pressure. 35 g N-benzyl-2-(2,2-dimethyl-1a,7b-dihydro-2H-oxireno[c]chromen-6-yl)acetamide was obtained as crude oil, which was used without further purification or characterization for the subsequent reaction.

C) 250 ml of a 25%-strength aqueous ammonia solution was added to a solution of 35 g of the N-benzyl-2-(2,2-dimethyl-1a,7b-dihydro-2H-oxireno[c]chromen-6-yl)acetamide obtained above in 250 ml ethanol, and the mixture was stirred for 18 hours at room temperature. The reaction mixture was poured into 500 ml water and extracted with 250 ml dichloromethane. The organic phase was separated, dried over sodium sulfate and largely evaporated under reduced pressure. 200 ml diethyl ether was added to the remaining residue. The crystals produced after a while were removed by suction and dried on a rotary evaporator at 60° C. and 20 bar. 11 g 2-(4-amino-3-hydroxy-2,2-dimethyl-3,4-dihydro-2H-chromen-6-yl)-N-benzylacetamide was obtained as grey solid, which was used without further purification or characterization for the subsequent reaction.

D) 4 ml of trimethylacetaldehyde was added to a solution of 11 g of the 2-(4-amino-3-hydroxy-2,2-dimethyl-3,4-dihydro-2H-chromen-6-yl)-N-benzylacetamide obtained above in 200 ml methanol. 2.44 g of NaBH$_3$CN was added in several portions, and the resulting suspension was stirred for 2 hours at 50° C. After cooling to room temperature, the reaction mixture was poured into 200 ml water. The aqueous phase was extracted once with 150 ml EA, the combined organic phases were dried over sodium sulfate, and the solvent was largely evaporated at reduced pressure. Chromatography of the remaining residue on silica gel (mobile phase: ethyl acetate/cyclohexane 1:1 v/v) and drying of the product fractions on a rotary evaporator yielded 10.8 g N-benzyl-2-[3-hydroxy-2,2-dimethyl-4-(neopentylamino)-3,4-dihydro-2H-chromen-6-yl]acetamide as colorless oil.

$^1$H-NMR (400 MHz, CDCl$_3$) δ [ppm]: 1.15 (s, 3H) 1.25 (t, 3H) 1.43 (s, 3H) 2.70 (q, 2H) 3.18-3.31 (3H) 3.55 (dd, 1H) 4.22 (dd, 1H) 4.30 (d, 2H) 5.51 (d, 1H) 5.81 (t, 1H) 6.56 (d, 1H) 6.67 (d, 1H) 6.96 (dd, 1H) 7.15 (m, 2H) 7.21-7.30 (3H) 7.32 (m, 2H) 7.84 (m, 2H); $^{13}$C-NMR (101 MHz, CDCl$_3$) δ [ppm]: 15.1 (q) 18.5 (q) 26.6 (q) 28.8 (t) 42.7 (t) 43.5 (t) 55.1 (d) 74.8 (d) 78.7 (s) 117.9 (d) 121.2 (s) 127.0 (s) 127.4 (d, 2 C) 127.5 (d, 3 C) 128.7 (d, 2 C) 128.9 (d, 3 C) 130.4 (d) 137.6 (s) 138.1 (s) 150.2 (s) 152.3 (s) 171.0 (s).

EXAMPLE 4

N-benzyl-2-{4-[[(4-ethylphenyl)sulfonyl](neopentyl)amino]-3-hydroxy-2,2-dimethyl-3,4-dihydro-2H-chromen-6-yl}acetamide

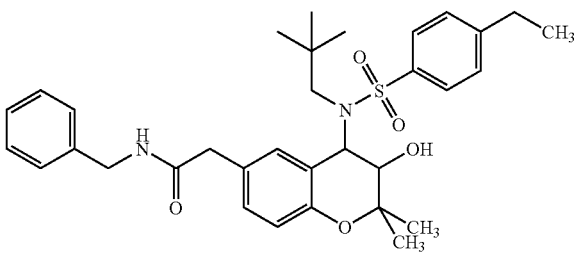

4.1 ml 4-ethyl benzenesulfonyl chloride was added dropwise to a solution of 10.8 g of the N-benzyl-2-[3-hydroxy-2,2-dimethyl-4-(neopentylamino)-3,4-dihydro-2H-chromen-6-yl]acetamide obtained above in Example 3 and 5 ml triethylamine in 100 ml dichloromethane. Dichloromethane was immediately substantially completely evaporated at reduced pressure, and the resulting reaction mixture was stirred for 90 minutes at 65° C. and 180 bar. The entire batch was poured into 150 ml water, and the aqueous phase was extracted once with 200 ml ethyl acetate. The solvent was largely evaporated at reduced pressure, the remaining residue was dried over sodium sulfate, and the remaining residue was chromatographed on silica gel (mobile phase: petroleum ether/ethyl acetate 3:1 v/v). Drying the product fractions in an oil pump vacuum yielded 3.6 g of the title compound (2 conformers) as colorless oil.

$^1$H-NMR (400 MHz, CDCl$_3$) δ [ppm]: 0.75 (s, 9H) 1.15 (s, 3H) 1.26 (t, 3H) 1.46 (s, 3H) 2.36 (1H) 2.65-2.75 (2H) 2.90-3.40 (4H) 3.86 (d,d 1H) 4.39 (d, 2H) 4.76 (d, 1H) 5.50 (t, 1H) 6.48 (1H) 6.73 (d, 1H) 7.03 (dd, 1H) 7.15-7.35 (7H) 7.81 (m, 2H) major; $^1$H-NMR (400 MHz, CDCl$_3$) δ [ppm]: 0.86 (s, 9H) 1.19 (s, 3H) 1.24 (t, 3H) 1.51 (s, 3H) 2.65-2.75 (2H) 2.81 (d, 1H) 3.25-3.60 (4H) 4.25-4.61 (4H) 4.60 (d,d 1H) 5.87 (t, 1H) 6.73 (d, 1H) 6.96 (dd, 1H) 7.15-7.35 (8H) 7.66 (m, 2H) minor; $^{13}$C-NMR (101 MHz, CDCl$_3$) δ [ppm]: 15.1 (q) 17.9 (q) 27.0 (q) 28.8 (q, 3C) 28.8 (t) 32.0 (s) 43.0 (t) 43.7 (t) 56.3 (t) 59.0 (d) 71.2 (d) 79.1 (s) 118.4 (d) 120.7 (s) 127.0-130.4 (12C) 137.2 (s) 138.1 (s) 150.4 (s) 153.0 (s) 170.7 (s) major; $^{13}$C-NMR (101 MHz, CDCl$_3$) δ [ppm]: 15.1 (q) 18.6 (q) 27.2 (q) 28.0 (q, 3C) 28.8 (t) 33.5 (s) 43.3 (t) 43.6 (t) 63.0 (t) 63.4 (d) 73.2 (d) 78.8 (s) 118.0 (d) 122.0 (s) 125.7-129.8 (12C) 137.3 (s) 138.3 (s) 150.2 (s) 151.8 (s) 171.3 (s) minor.

EXAMPLE 5

N-(4-chlorobenzyl)-2-(3-hydroxy-2,2-dimethyl-4-{[(3-methylphenyl)sulfonyl]amino}-3,4-dihydro-2H-chromen-6-yl)acetamide

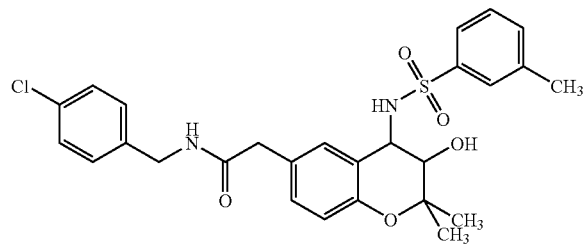

A) 175.6 g methyl-4-hydroxyphenylacetate and 128.9 g phenylboronic acid were added to 3.5 l m-xylene. 88.9 g 3-methylbut-2-enal, and 130 ml of glacial acetic acid were added to this mixture. The mixture was heated to 140° C. in a Dean-Stark apparatus under a nitrogen atmosphere until approximately 70% of the phenol had reacted (approximately 48-72 hours). Then the reaction mixture was allowed to cool to room temperature, the mixture was filtered, and the solvent was evaporated at reduced pressure. The remaining residue was dissolved in a 1:1 mixture of tetrahydrofuran (THF) and a 25%-strength aqueous ammonia solution (v/v) and stirred for 2 hours. The THF was largely evaporated off at reduced pressure and ethyl acetate was added. The organic phase was separated, washed in succession with an aqueous 1 N NaOH and a saturated aqueous common salt solution and finally dried over sodium sulfate. The solvent was largely evaporated at reduced pressure, and the remaining residue was chromatographed on silica gel (mobile phase: n-hexane/EA 15:1 to 10:1 v/v). Drying of the product fractions in an oil pump vacuum yielded 106 g methyl-(2,2-dimethyl-2H-chromen-6-yl)acetate as pale yellow oil, which was used without further characterization for the subsequent reaction.

B) 106 g of the methyl-(2,2-dimethyl-2H-chromen-6-yl)acetate obtained above was dissolved in 900 ml THF. A solution of 57.6 g LiOH in 900 ml water was added to this receiving solution, and the mixture was stirred for 16 hours at room temperature. The THF was largely evaporated at reduced pressure, and the aqueous residue was acidulated by addition of an aqueous 6N hydrochloric acid solution. The aqueous phase was extracted with ethyl acetate, and the combined organic phases were washed in succession with a saturated aqueous common salt solution and with water. The organic phase was dried over sodium sulfate, and the solvent was then substantially completely evaporated in a vacuum. 97.6 g 2,2-(dimethyl-2H-chromen-6-yl)-acetic acid was obtained, which was used without further purification or characterization for the subsequent reaction.

C) 14.0 g of the 2,2-(dimethyl-2H-chromen-6-yl)acetic acid obtained above and 13.54 g EDC×HCl were dissolved in dichloromethane at room temperature. 10.0 g of 4-chlorobenzylamine was added dropwise to this receiving solution with stirring, and the mixture was stirred for 16 hours at room temperature. Then the reaction mixture was washed in succession with water, 1N aqueous hydrochloric acid solution and saturated aqueous common salt solution, and the organic phase was dried over sodium sulfate. Evaporation of the solvent at reduced pressure and drying of the remaining residue in an oil pump vacuum yielded 21.92 g of the crude N-4-chlorobenzyl-2-(2,2-dimethyl-2H-chromen-6-yl) acetamide, which was used without further purification or characterization for the subsequent reaction.

D) 700 ml of a saturated aqueous sodium hydrogen carbonate solution was added to a solution of 21.92 g of the N-4-chlorobenzyl-2-(2,2-dimethyl-2H-chromen-6-yl) acetamide obtained above in 600 ml dichloromethane. A total of 31.6 g MCPBA (72%) was added in portions to this receiving solution and stirred for 16 hours at room temperature. The organic phase was separated, washed twice with a 5%-strength aqueous sodium hydrogen carbonate solution, dried over sodium sulfate and substantially completely evaporated at reduced pressure. Drying in an oil pump vacuum yielded N-(4-chlorobenzyl)-2-(2,2-dimethyl-1a,7b-dihydro-2H-oxireno[c]chromen-6-yl)acetamide as crude oil, which was used without further purification or characterization for the subsequent reaction.

E) The N-(4-chlorobenzyl)-2-(2,2-dimethyl-1a,7b-dihydro-2H-oxireno[c]chromen-6-yl) acetamide obtained above was immediately poured into a mixture of so much ethanol and 25%-strength aqueous ammonia solution (6:5 v/v) that a 0.2 M solution of the compound was obtained, and the resulting solution was stirred for 16 hours at 50° C. Then the solution was allowed to cool to room temperature, and the solvent was largely evaporated at reduced pressure. The remaining residue was chromatographed on silica gel (mobile phase: gradient dichloromethane/methanol/25%-strength aqueous ammonia solution 97.5:2:0.5 to 90:9.5:0.5 v/v/v). Drying of the product fractions yielded 7.3 g 2-(4-amino-3-hydroxy-2,2-dimethyl-3,4-dihydro-2H-chromen-6-yl)-N-4-chlorobenzyl acetamide, which was used without further purification for the subsequent reaction. The other regioisomer, 2-[3-amino-4-hydroxy-2,2-dimethylchromen-6-yl]-N-4-chlorobenzyl acetamide, was not observed.

F) 15 mg PS-methylpiperidine and a solution of 6.0 mg 3-methylbenzenesulfonyl chloride in 0.5 ml dichloromethane were added in succession in a sample well of a sample plate for automatic parallel synthesis to a solution of 9 mg of the 2-(4-amino-3-hydroxy-2,2-dimethyl-3,4-dihydro-2H-chromen-6-yl)-N-4-chlorobenzyl acetamide obtained above in 0.5 ml dichloromethane. The sample plate was shaken for 40 hours at room temperature, and then 20 mg AMPS was added to the well. The plate was shaken for a further 16 hours at room temperature before the liquid reaction phase was separated from the resin, and the resin was washed twice with 1 ml portions of dichloromethane. The solvent of the combined organic phases was evaporated at reduced pressure, and the title compound was obtained in a purity of 95% (determination by HPLC-MS), [M+H]$^+$ 529.

EXAMPLE 6

N-butyl-2-{(4-[[(2,5-dimethoxyphenyl)sulfonyl](2-ethylbutyl) amino]-3-hydroxy-2,2-dimethyl-3,4-dihydro-2H-chromen-6-yl}acetamide

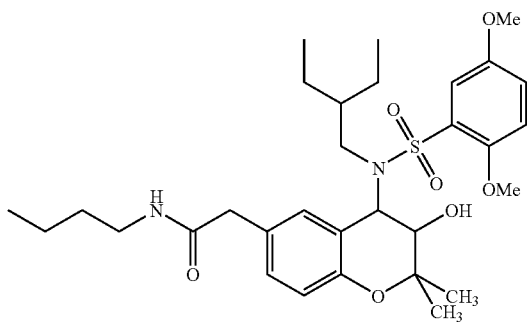

A) 10.0 g 2,2-(dimethyl-2H-chromen-6-yl)acetic acid (for preparation see Example 5B)), 9.67 g EDC×HCl and 5.41 g n-butylamine were reacted according to the procedure set forth in Example 5C). 17.5 g crude N-(n-butyl)-2-(2,2-dimethyl-2H-chromen-6-yl)acetamide was obtained, which was used without further purification or characterization for the subsequent reaction.

B) 700 ml of a saturated aqueous sodium hydrogen carbonate solution was reacted with a solution of 17.5 g of the N-(n-butyl)-2-(2,2-dimethyl-2H-chromen-6-yl)acetamide obtained above in 600 ml dichloromethane and 31.6 g MCPBA (72%) in a manner corresponding to the procedure of Example 5D). The crude N-butyl-2-(2,2-dimethyl-1a,7b-dihydro-2H-oxireno[c]chromen-6-yl)acetamide was obtained, which was used immediately without further purification or characterization for the subsequent reaction.

C) The n-butyl-2-(2,2-dimethyl-1a,7b-dihydro-2H-oxireno[c]chromen-6-yl) acetamide obtained above was immediately poured into a mixture of so much ethanol and 25%-strength aqueous ammonia solution (6:5 v/v) that a 0.2 M solution of the compound was obtained and was processed further in a manner corresponding to the procedure of Example 5E). 7.4 g 2-(4-amino-3-hydroxy-2,2-dimethyl-3,4-dihydro-2H-chromen-6-yl)-N-(n-butyl)acetamide was obtained, which was used without further purification for the subsequent reaction. The other regioisomer, 2-[3-amino-4-hydroxy-2,2-dimethylchromen-6-yl]-N-(n-butyl)acetamide, was not observed.

D) 610 mg of the 2-(4-amino-3-hydroxy-2,2-dimethyl-3,4-dihydro-2H-chromen-6-yl)-N-(n-butyl)acetamide obtained above was dissolved in 20 ml tetrahydrofuran (THF) and 220 µl TMOF was added. Then 197 mg ethyl butyraldehyde was added to this receiving solution, and the reaction mixture was shaken for 16 hours at room temperature. The solvent was removed at reduced pressure, the remaining residue was taken up with 20 ml methanol, 7.9 g PS—BH$_4$ was added, and the reaction mixture was shaken for a further 16 hours at room temperature. The reaction mixture was then filtered, and the reactive resin was washed with methanol. The combined filtrates were largely evaporated at reduced pressure, the remaining residue was dissolved in 20 ml dichloromethane, and 0.4 equivalents of a known polymer-supported aldehyde (PS—CHO) and 0.6 equivalents of AMPS were added in succession. The mixture was shaken again for 16 hours at room temperature, the liquid phase was filtered off from the reactive resin, and the resin was subsequently washed with THF. The combined liquid organic phases were evaporated at reduced pressure, and 572 mg of 95% pure (determination by HPLC) 2-[4-(2-ethylbutylamino)-3-hydroxy-2,2-dimethylchromen-6-yl]-N-(n-butyl)acetamide was obtained which was used without further purification or characterization for the subsequent reaction.

E) 20 mg PS-methylpiperidine resin and a solution of 37.1 mg 3,5-dimethoxybenzenesulfonyl chloride in 0.4 ml dichloromethane were added successively to in a sample well of a sample plate for automatic parallel synthesis containing a solution of 14.8 mg of the 2-[4-(2-ethylbutylamino)-3-hydroxy-2,2-dimethylchromen-6-yl]-N-(n-butyl) acetamide obtained above in 0.6 ml dichloromethane. The mixture was shaken for 168 hours at room temperature, the resin was filtered out, and then 120 mg PS-AMPS was added to the filtrate. It was shaken for a further 16 hours at room temperature before the liquid reaction phase was separated from the resin, and the resin was washed twice with 1 ml portions of dichloromethane. The solvent of the combined organic phases was evaporated at reduced pressure, and the title compound was obtained in a purity of 96% (determination by HPLC-MS), [M+H]$^+$ 591.

The compounds of Formula I listed in the following Table 6 can also be prepared according to the processes described in the foregoing examples or analogously thereto.

TABLE 6

| | | | | Further compounds of Formula I: | | | | |
|---|---|---|---|---|---|---|---|---|
| Ex. No. | R$^1$ | R$^2$ | R$^3$ | R$^4$ | R$^5$ | R$^6$ | *C-3 | *C-4 |
| 7 | Me | Me | 4-ethylphenyl | neopentyl | H | benzyl | S | R |
| 8 | Me | Me | 4-ethylphenyl | neopentyl | H | benzyl | R | S |
| 9 | Me | Me | 4-ethylphenyl | H | H | (S)-tetrahydronaphth-1-yl | S | R |

TABLE 6-continued

Further compounds of Formula I:

| Ex. No. | R¹ | R² | R³ | R⁴ | R⁵ | R⁶ | *C-3 | *C-4 |
|---|---|---|---|---|---|---|---|---|
| 10 | Me | Me | 4-ethylphenyl | neopentyl | H | phenylethyl | trans | |
| 11 | Me | Me | 4-ethylphenyl | H | H | benzyl | S | R |
| 12 | Me | Me | 4-ethylphenyl | H | H | phenylethyl | trans | |
| 13 | Me | Me | 3-fluorophenyl | H | H | (S)-tetra-hydronaphth-1-yl | trans | |
| 14 | Me | Me | phenyl | H | H | (S)-tetra-hydronaphth-1-yl | trans | |
| 15 | Me | Me | 4-methylphenyl | H | H | (S)-tetra-hydronaphth-1-yl | trans | |
| 16 | Me | Me | 4-ethylphenyl | H | —[(CH₂)₂]₂N—C₆H₅ | | trans | |
| 17 | Me | Me | 4-iodophenyl | H | | n-butyl | trans | |
| 18 | Me | Me | 4-methylphenyl | cyclopropylmethyl | H | benzyl | trans | |
| 19 | Me | Me | 4-methylphenyl | 3-methylbutyl | H | benzyl | trans | |
| 21 | Me | Me | 2,5-dimethoxyphenyl | 2-ethylbutyl | H | 2-furylmethyl | trans | |
| 22 | Me | Me | 3-methoxyphenyl | n-pentyl | H | 1,2-dimethylpropyl | trans | |
| 23 | Me | Me | 4-trifluoromethylphenyl | 3-methylbutyl | H | benzyl | trans | |
| 24 | Me | Me | 3-chloro-4-fluorophenyl | 2-methylpropyl | H | n-propyl | trans | |
| 25 | Me | Me | 2-naphthyl | 3-methylbutyl | H | benzyl | trans | |
| 26 | Me | Me | 4-biphenyl | 3-methylbutyl | H | n-propyl | trans | |
| 27 | Me | Me | 3-methoxyphenyl | 3-methylbutyl | H | 4-chlorobenzyl | trans | | trans = trans position of the substituents at C-3 and C-4, but mixture of the stereoisomers; Me = methyl; "S" and "R" each relate to the absolute configuration on the corresponding carbon.

EXAMPLE I

Capsules Containing 2-(4-{[(4-ethylphenyl)sulfonyl]amino}-3-hydroxy-2,2-dimethyl-3,4-dihydro-2H-chromen-6-yl)-N-1,2,3,4-tetrahydronaphth-1-yl Acetamide Capsules with the following composition per capsule were prepared:

| | |
|---|---|
| 2-(4-{[(4-ethylphenyl)sulfonyl]amino}-3-hydroxy-2,2-dimethyl-3,4-dihydro-2H-chromen-6-yl)-N-1,2,3,4-tetrahydronaphth-1-yl acetamide | 20 mg |
| Corn starch | 60 mg |
| Lactose | 300 mg |
| Ethyl acetate | q.s. |

The active substance, the corn starch and the lactose were processed into a homogenous pasty mixture using the ethyl acetate. The paste was ground, and the resulting granules were placed on a suitable tray and dried at 45° C. in order to remove the solvent. The dried granules were passed through a crusher and mixed in a mixer with the following additional auxiliaries:

| | |
|---|---|
| Talcum | 5 mg |
| Magnesium stearate | 5 mg |
| Corn starch | 9 mg |
| and then filled into 400 mg capsules (= capsule size 0). | |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A compound corresponding to formula I:

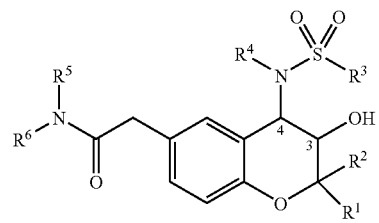

wherein
R¹ is $C_{1-4}$-alkyl,
R² is $C_{1-4}$-alkyl,
R³ is phenyl which is optionally substituted 1 or 2 times by halogen, $c_{1-4}$-alkyl, $C_{1-4}$-alkoxy or trifluoromethyl; naphthyl or biphenyl,
R⁴ is hydrogen; $C_{1-6}$-alkyl or $C_{3-7}$-cycloalkyl-$C_{1-4}$-alkyl,
R⁵ is hydrogen, and
R⁶ is $C_{1-6}$-alkyl; phenyl-$C_{1-4}$-alkyl, the phenyl group of which is optionally substituted once by halogen; furyl-$C_{1-4}$-alkyl or tetrahydronaphthyl, or
R⁵ and R⁶, together with the nitrogen to which they are bonded, form a piperazine ring which may optionally be substituted by phenyl.

2. A compound according to claim 1, wherein R¹ and R² are each methyl.

3. A compound according to claim 1, wherein R³ is phenyl or mono-substituted phenyl.

4. A compound according to claim 1, wherein R⁴ is hydrogen, $C_{1-6}$-alkyl or cyclopropyl-$C_{1-4}$-alkyl.

5. A compound according to claim 1, wherein R⁶ is phenyl-$C_{1-4}$-alkyl or tetrahydronaphthyl.

6. A compound according to claim 1, wherein in the pyran ring the C-3 carbon bearing the hydroxy substituent is in the S configuration and t he C-4 carbon bearing the nitrogen-containing substituent is in the R configuration.

7. A compound according to claim 1, selected from the group consisting of:
- 2-(4-{[(4-ethylphenyl)sulfonyl]amino}-3-hydroxy-2,2-dimethyl-3,4-dihydro-2H-chromen-6-yl)-N-1,2,3,4-tetrahydronaphthalen-1-yl acetamide;
- 2-((3S,3R)-4-{[(4-ethylphenyl)sulfonyl]amino}-3-hydroxy-2,2-dimethyl-3,4-dihydro-2H-chromen-6-yl)-N-[(1R)-1,2,3,4-tetrahydronaphthalen-1-yl]acetamide;
- N-benzyl-2-{4-[[(4-ethylphenyl)sulfonyl](neopentyl)amino]-3-hydroxy-2,2-dimethyl-3,4-dihydro-2H-chromen-6-yl}acetamide;
- 2-{4-[[(4-ethylphenyl)sulfonyl](neopentyl)amino]-3-hydroxy-2,2-dimethyl-3,4-dihydro-2H-chromen-6-yl}-N-(2-phenylethyl) acetamide, and
- 2-(4-{[(4-methylphenyl)sulfonyl]amino}-3-hydroxy-2,2-dimethyl-3,4-dihydro-2H-chromen-6-yl)-N-1,2,3,4-tetrahydronaphthalen-1-yl acetamide.

8. A composition comprising a compound according to claim 1, and at least one pharmaceutical auxiliary or carrier.

9. A process for preparing a compound corresponding to Formula I:

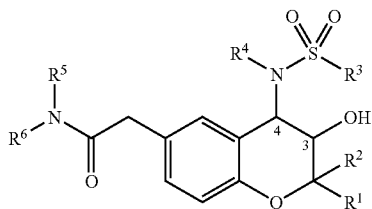

I wherein
- $R^1$ is $C_{1-4}$-alkyl,
- $R^2$ is $C_{1-4}$-alkyl,
- $R^3$ is phenyl which is optionally substituted 1 to 2 times by halogen, $C_{1-4}$-alkyl, $C_{1-4}$-alkoxy or trifluoromethyl; naphthyl or biphenyl,
- $R^4$ is hydrogen; $C_{1-6}$-alkyl or $C_{3-7}$-cycloalkyl-$C_{1-4}$-alkyl,
- $R^5$ is hydrogen, and
- $R^6$ is $C_{1-6}$-alkyl; phenyl-$C_{1-4}$-alkyl, the phenyl group of which is optionally substituted once by halogen; furyl-$C_{1-4}$-alkyl or tetrahydronaphthyl, or
- $R^5$ and $R^6$, together with the nitrogen to which they are bonded, form a piperazine ring which may optionally be substituted by phenyl, said method comprising reacting a compound corresponding to formula II:

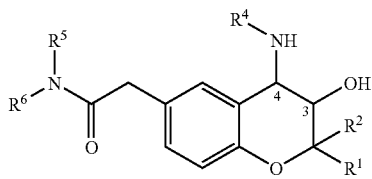

II wherein $R^1$, $R^2$, $R^4$, $R^5$ and $R^6$ have the above meanings, with a compound corresponding to formula III:

$$X—SO_2—R^3$$

III wherein $R^3$ has the above meaning, and X is a cleavable leaving group.

10. A compound corresponding to formula II:

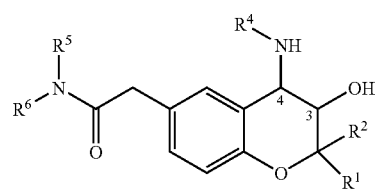

II wherein
- $R^1$ is $C_{1-4}$-alkyl,
- $R^2$ is $C_{1-4}$-alkyl,
- $R^4$ is hydrogen; $C_{1-6}$-alkyl or $C_{3-7}$-cycloalkyl-$C_{1-4}$-alkyl,
- $R^5$ is hydrogen, and
- $R^6$ is $C_{1-6}$-alkyl; phenyl-$C_{1-4}$-alkyl, the phenyl group of which is optionally substituted once by halogen; furyl-$C_{1-4}$-alkyl or tetrahydronaphthyl, or
- $R^5$ and $R^6$, together with the nitrogen to which they are bonded, form a piperazine ring which may optionally be substituted by phenyl.

11. A compound corresponding to formula I:

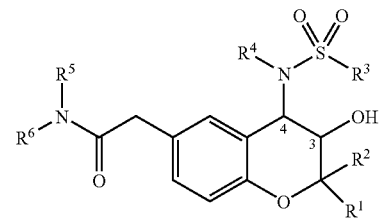

I wherein
- $R^1$ is $C_{1-4}$-alkyl,
- $R^2$ is $C_{1-4}$-alkyl,
- $R^3$ is phenyl which is substituted 1 or 2 times by halogen or $C_{1-4}$-alkyl,
- $R^4$ is hydrogen or $C_{1-6}$-alkyl,
- $R^5$ is hydrogen, and
- $R^6$ is $C_{1-6}$-alkyl or tetrahydronaphthyl.

* * * * *

UNITED STATES PATENT AND TRADEMARK OFFICE
CERTIFICATE OF CORRECTION

PATENT NO. : 7,368,582 B2  Page 1 of 1
APPLICATION NO. : 10/961368
DATED : May 6, 2008
INVENTOR(S) : David Sykes et al.

It is certified that error appears in the above-identified patent and that said Letters Patent is hereby corrected as shown below:

Column 9, lines 2 and 3, "(= "Chinese hamster oocytes", "CHO")" should read
-- (="Chinese hamster ovary cells", "CHO") --.

Column 9, line 8, "oocytes" should read -- ovary cells --.

Column 9, line 9, "oocytes" should read -- ovary cells --.

Column 9, line 11, "oocytes" should read -- ovary cells --.

Column 9, line 13, "oocytes" should read -- ovary cells --.

Column 9, line 15, "oocytes" should read -- ovary cells --.

Column 9, line 19, "oocytes" should read -- ovary cells --.

Column 9, line 25, "Chinese hamster oocytes" should read -- Chinese hamster ovary cells --.

Column 9, line 28, "oocytes" should read -- ovary cells --.

Column 9, line 29, "ooctyes" should read --ovary cells --.

Column 9, line 44, "oocytes" should read -- ovary cells --.

Column 10, line 4, "oocytes" should read -- ovary cells --.

Column 10, line 35, "ooctyes" should read -- ovary cells --.

Column 10, line 50, "oocytes" should read -- ovary cells --.

Column 10, line 61, "ooctyes" should read -- ovary cells --.

Signed and Sealed this

Nineteenth Day of January, 2010

David J. Kappos
*Director of the United States Patent and Trademark Office*